United States Patent [19]

King

[11] Patent Number: Plant 6,748

[45] Date of Patent: Apr. 18, 1989

[54] ROSE PLANT/KINSCHOON

[76] Inventor: Gene King, 3711 Caddo St., Monroe, La. 71203

[21] Appl. No.: 116,279

[22] Filed: Nov. 2, 1987

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by red/yellow color blend of the buds and flowers and by the profusion of bloom.

1 Drawing Sheet

The present invention relates to a new and distinct variety of hardy, dwarf, bush type rose plant of the miniature class; the variety being primarily characterized — as to novelty — by red yellow (red blend) buds and flowers which in general color effect are similar to Over The Rainbow (miniature — U.S. Plant Pat. No. 3,472) but lighter red.

The variety is further characterized by:

An abundance of bloom, with flowers, on mature plant, usually borne singly or in clusters or sprays.

Little or no fragrance.

A plant which is vigorous, of somewhat spreading shape with matt, small foliage with pointed leaflets; the buds and flowers being similar in form to Dreamglo (miniature — U.S. Plant Pat. No. 4,579).

The plant, which has a normal weight of 12 inches or more and a slightly broader spread, can easily be maintained at lesser height or width by occasional trimming.

A plant which grows and blooms satisfactorily both in greenhouse and outdoors; is good for growing in pots or hanging baskets; and provides excellent garden decoration as well as cut flowers.

The present variety of miniature rose was originated by me at my nursery located at Monroe, La., under conditions of careful control and observation as a cross between Little Darling (floribunda — U.S. Plant Pat. No. 1,581) as the seed parent and Poker Chip (miniature — U.S. Plant Pat. No. 4,582), as the pollen parent.

Subsequent to origination of the variety I successfully reproduced it at my nursery located aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being be reference to British Colour Council Horticultural Colour Chart, except where common terms of color definition are employed.

Type: Hardy; dwarf; bushy; spreading; seedling; greenhouse; outdoors; cut flowers; garden decoration; potted plant.

Class: Miniature.

*International indentification.*—Variety: Kinschoon.

*Commercial synonym.*—Prairie Schooner.

Flowers borne: Usually singly (sometimes several together) on slender wirey stems.

Quantity of bloom: Abundant both outside and in greenhouse.

Bud:

*Peduncle.*—Medium to long; slender but sturdy; erect; medium green, sometimes tinted bronze (outdoors).

*Hairs.*—Very short (morelike fuzz). Before calyx breaks; size — small. Form long; pointed with several foliaceous apendages and several hairs on surface of bud; with foliaceous parts extending beyond the tipof the bud equal to one-half or less of its length. Note: The fine hairs on peduncle and bud can only be seen with the aid of a reading glass.

*Color.*—Medium green, occasionally tinted with bronze (outdoors). As calyx breaks, color — red. Opening: opens well in all weather.

Bloom:

*Size when fully open.*—Small, averaging about 30 mm (1½").

*Petalage.*—Double — averaging about 25 petals, arranged regularly. Form — high centered, becoming more open as flower matures, with petals reflexing loosely outward. Open flowers show stamens.

Petals: Fairly thick; satiny on inside and on outside surfaces.

*Shape.*—outside petals, broad lanceolate with pointed tip; intermediate — broad lanceolate with rounded tip; inside — similar to intermediate petal but narrower.

Color: Newly opened flower from a plant grown in plastic greenhouse (October 1987).

*Outside petal.*—Outside surface — near Empire Yellow 603/3 (sometimes slightly deeper yellow at base) and near crimson 22 at tip. Inside surface — near Empire Yellow 603 on basal ⅓ and near crimson 22 on next ⅔.

*Intermediate petal.*—Outside surface — similar to outside petal. Inside surface — similar to inside petal.

*Inner petal.*—Outside surface — same as intermediate petal; inside surface — same as intermediate petal. General color effect; newly opened flowers — bright crimson to yellow at base. Three days open — color similar to but lighter than newly opened flowers. Behavior — opens well in all weather. Color lasts well. Spent petals drop off. Flower longevity (October 1987) — plant in pot 4–5 days or longer. Cut flowers at living room temperature 3–4 days.

Reproductive organs:

*Stamens.*—Abundant, arranged regularly about pistils.

*Filaments.*—Varying length, medium to short length, yellow.

*Anther.*—Well formed; yellow.

*Pollen.*—Large amount.

*Pistils.*—Average number.

*Styles.*—Fairly even; medium to short length; bunched; color — red.

*Ovaries.*—All enclosed in calyx.

*Hips.*—None to few.

*Sepals.*—Permanent; spear shaped; recurved against peduncle.

*Seed.*—Few or none.

Foliage:

*Leaves.*—Compound of five (sometimes three or seven leaflets; fairly small; leathery; matt.

*Leaflets.*—Shape: broad lanceolate; nearly oval; apex acute; base rounded or rounded acute. Margin serrate. Color: medium to dark green; new growth — norma (medium green). Rachis: medium strength; upperside may have a few tiny short prickles or hairs, grooved; underside sparsely thorny with few or no tiny prickles. Stipules: medium long to long; narrow to medium width; short length; narrow points which turn out usually at about 45 degrees.

Growth:

*Habit.*—Dwarf; bushy; spreading; much branched.

*Growth.*—Free vigorous; internodes short.

*Canes.*—Medium; slender; sturdy.

*Thorns.*—Average; slender nearly straight, inclined slightly downward; color; brown. Prickles — noe.

*Branches.*—Color: medium green. Thorns: moderate number; medium length; slender; straight. Medium oval bse. Prickles: none. Hairs — none.

The miniature rose plant and its flowers as herein described may vary in slight detail due to climatic, soil and cultural conditions under which the variety may be grown; the resent description being of the variety as grown at Monroe, La.

The following is claimed:

1. A new and distinct variety of miniature rose plant of hardy, dwarf, bushy, spreading, much branched habit, substantially as illustrated and described, characterized by buds and flowers of a generally apricot yellow color, being of a shade generally near Empire Yellow 603/1 but modified by red coloring to give an apricoty effect; and further characterized by a plant of vigorous and compact growth habit, easy to propagate from cuttings or by budding, with an abundance of small to medium size matt foliage and an abundance of flowers borne usually singly but sometimes in clusters or spray.

* * * * *

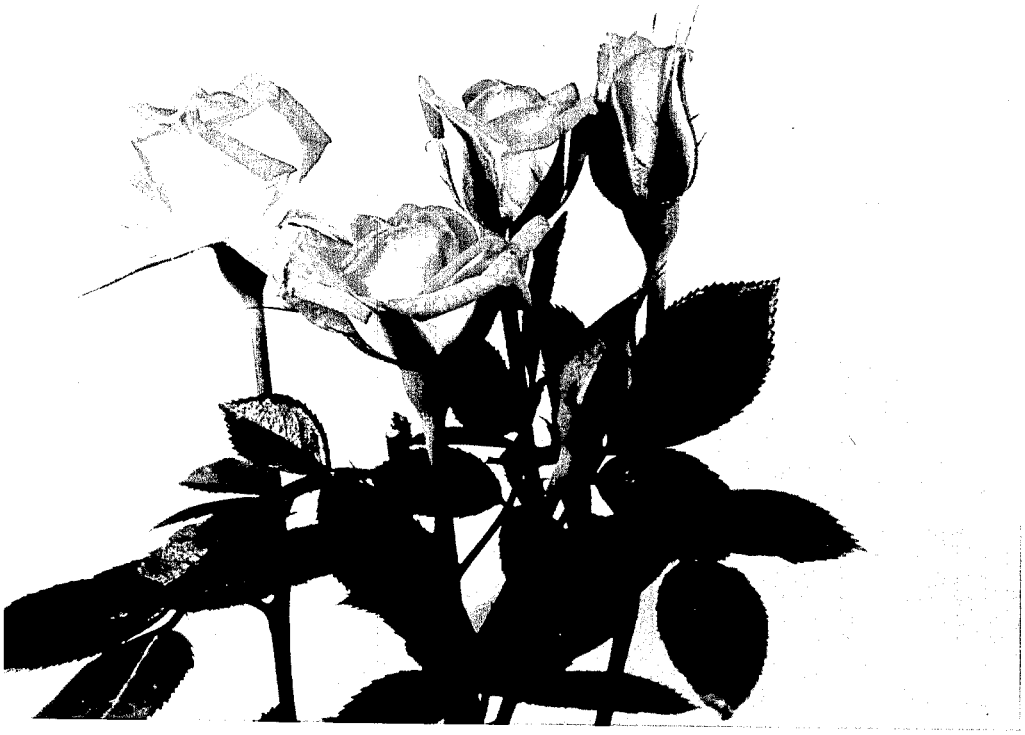

U.S. Patent Apr. 18, 1989 Plant 6,748